United States Patent [19]

Adamich et al.

[11] Patent Number: 4,737,276

[45] Date of Patent: Apr. 12, 1988

[54] APPARATUS FOR MANUFACTURING LIPOSOMES

[75] Inventors: Marina Adamich, Boothwyn, Pa.; David T. Bach, Wilmington, Del.

[73] Assignee: E. I. Du Pont de Nemours and Company, Wilmington, Del.

[21] Appl. No.: 883,318

[22] Filed: Jul. 8, 1986

Related U.S. Application Data

[62] Division of Ser. No. 684,947, Dec. 21, 1984, Pat. No. 4,622,188.

[51] Int. Cl.[4] .............................................. B01D 13/00
[52] U.S. Cl. ............................... 210/96.2; 210/321.72; 210/321.83
[58] Field of Search ................. 422/239, 62, 108, 110, 422/111; 210/96.2, 321.1, 321.2, 321.3, 94; 264/4.6; 436/829; 424/38

[56] References Cited

U.S. PATENT DOCUMENTS

| | | | |
|---|---|---|---|
| 3,349,913 | 10/1967 | Schneider | 210/96.2 X |
| 3,606,539 | 9/1971 | Polanyi et al. | 210/96.2 X |
| 3,652,861 | 3/1972 | Engholt | 210/96.2 X |
| 3,757,947 | 9/1973 | Wakefield et al. | 210/321.2 X |
| 3,832,067 | 8/1974 | Kopf et al. | 210/96.2 X |
| 3,961,898 | 6/1976 | Heely et al. | 210/96.2 X |
| 4,016,100 | 4/1977 | Suzuki et al. | 264/413 |
| 4,118,315 | 10/1978 | Fletcher | 210/96.2 X |
| 4,133,874 | 1/1979 | Miller et al. | 424/38 |
| 4,153,554 | 5/1979 | Heide et al. | 210/321.2 X |
| 4,181,610 | 1/1980 | Shintani et al. | 210/96.2 X |
| 4,242,460 | 12/1980 | Chick et al. | 210/497.1 X |
| 4,372,949 | 2/1983 | Kodama et al. | 514/78 |
| 4,452,747 | 6/1984 | Gersonde et al. | 264/441 |
| 4,500,430 | 2/1985 | Dasgupta | 210/497.1 X |

OTHER PUBLICATIONS

Liposome-Mediated Immunoassays for Small Haptens (Digoxin) Independent of Complement, Freytag & Litchfield, Journal of Immunological Methods, 70 (1984), 133–140, Elsevier Science Publishers B.V.
Mimms; L. R. et al., Biochemistry (1981), 20,833.
Zumbuehl; O. and H. G. Weder, Biochim et Biophysics Acta (1981), 640,252.
Rhoden; B. V. and S. M. Goldin, Biochemistry (1981), 18,4173.
DeLoach; J. R. et al., Analytical Biochemistry (1980), 102,220.
Milsmann; M. H. W. et al., Biochim et Biophys. Acta (1978), 512,147.
Lipoprep: Dianorm, Diachema Ag. Ruschl Ikon/-Zurich (1980).
MFC. Microfluids Corp., div. Biotechnology Development Corp., 44 Mechanic St., Newton, MA 02164 (undated).

Primary Examiner—Frank Spear

[57] ABSTRACT

An apparatus for manufacturing liposomes is characterized by optically monitoring the light transmission of a liposome precursor solution and controlling the flow rate and/or temperature of the precursor solution and/or a dialysis buffer solution in accordance therewith.

13 Claims, 3 Drawing Sheets

APPARATUS FOR MANUFACTURING LIPOSOMES

This is a division of application Ser. No. 684,947, filed Dec. 21, 1984, now U.S. Pat. No. 4,622,188, issued Nov. 11, 1986.

BACKGROUND OF THE INVENTION

The present invention relates to an apparatus for manufacturing uniform, bilayer vesicles, or liposomes, using either the batch/flow or continuous flow processes.

Liposomes are phospholipid bilayers surrounding an aqueous compartment. Their dimensions range from 0.20 microns to over ten microns in diameter. They may comprise a single bilayer of lipid, a so-called unilamellar vesicle, or they may contain multiple bilayers interspaced by an aqueous phase, or so-called multilamellar vesicles. Liposomes are uniquely suited as carriers for drugs, biological molecules such as DNA, proteins and non-biological molecules such as carboxyfluorescein. These materials can be encapsulated in the interior aqueous spaces of the liposome or they may be inserted in or attached to the lipid bilayers which bound and limit the internal aqueous space. Unilamellar vesicles are often preferred to multilamellar vesicles because of their size, biocompatibility and defined internal space.

Commonly utilized manufacturing procedures for the preparation of liposomes include the simple dispersion of dried phospholipids in an aqueous media using a homogenizer. This procedure results in the formation of multilamellar liposomes. These multilamellar liposomes may be converted to unilamellar liposomes by ultrasonic irradiation or by passage through filters under pressure. Lipids in organic solutions can be injected into an aqueous media. This often results in the formation of unilamellar vesicles.

Many biological molecules to be entrapped are not compatible with organic solvents. Accordingly, another procedure for liposome formation is the detergent batch dialysis method. This method incorporates the co-micellization of lipids with a detergent having a high critical micelle concentration. A micelle is an optically transparent species which is soluble in water. The material to be incorporated is added simultaneously and usually remains in bulk aqueous phase it it is hydrophillic but incorporates into the mixed micelle if it is hydrophobic. The mixture is placed into a suitable dialysis vessel, one boundary of which is defined by a dialysis membrane, and the detergent is removed by dialysis. As the detergent is removed, the lipids, which have a very low critical micelle concentration, remain behind and thermodynamically rearrange themselves into unilamellar vesicles. The detergent batch dialysis procedure is relatively mild with the detergent of choice being typically octyl-D-glucoside which is biocompatible. Typically the batch dialysis method places a volume of the liposome precursor solution in a dialysis bag which forms the vessel alluded to above. The dialysis bag is itself immersed in a volume of a dialysis buffer solution. The entire volume of the buffer is periodically changed.

Several disadvantages are encountered with either of the commonly practiced techniques for producing liposomes. These disadvantages include vesicle rupture due to mechanical stress, size inhomogeneity, excessive time for vesicle formation, limited internal volume of liposomes, inconsistent encapsulation of material, liposomes which may be unstable, dilution of reagents, and temperature effects causing a general lack of reproducibility.

Two commercial instruments are presently available which attempt to circumvent some of the above-listed problems. These two instruments are the LIPOPREP produced by Dianorm, Diachema AG, Rushilkon, Switzerland, and the MICROFLUIDIZER produced by Microfluids Development Corporation, a division of Biotechnology Development Corporation, Newton, Mass.

The first instrument is a batch/flow dialysis unit which removes detergent from detergent/phospholipid mixed micelle solution by a continuous flow of the buffer across two membranes between which is disposed a stationary volume of the mixed micelle solution. The instrument allows for variable flow rates for dialysis and provides a temperature control unit which can be added. The liposomes are prepared in the batch dialysis mode and can produce up to six milliliters of liposomes in up to twenty-four hours. The disadvantage of this instrument is perceived to be the long dialysis time for a small volume of liposomes produced.

The second instrument effects a continuous manufacture of liposomes and microemulsions. The basic device includes a reservoir containing multilamellar vesicles previously prepared by homogenization or by other means and a high pressure unit which propels the multilamellar vesicles through filters for sizing. The filters are changeable as desired. A volume greater than fifteen milliliters can be produced within minutes. The disadvantages of this instrument are perceived to be the lack of temperature control resulting in inherent heating of the equipment during usage, large dead spaces unavailable for dialysis, variance in liposome homogeneity concerning size and internal volumes, and liposome stability. Moreover, the high pressure used can shear the sensitive vesicle damaging molecules such as DNA and other biopolymers. The manufacturing procedure using this instrument is a two-step method which first requires the formation of multilamellar vesicles.

Of the two manufacturing procedures, as represented by the above instruments currently in use, that based on the detergent batch/flow dialysis is perceived as being the most reproducible, is the most mild in the sense that it maintains molecular activity and is the method by which detergent can be most effectively removed. However, it has not been possible yet to accurately define the condition for maximum encapsulation of reagents, high reproducibility, minimization of dialysis time and requisite detergent levels due to lack of data on the kinetics for liposome formation. Thus, consistent manufacturability of liposomes for commercial purposes is not maximized.

In view of the foregoing, it is believed advantageous to provide an apparatus and method for liposome manufacture which allows for real-time kinetic data acquisition of liposome formation. The apparatus and method is believed most desirably practiced by the incorporation of an optical monitoring system which measures light transmission level of the liposomes forming within the liposome precursor solution. Thus, the system and method can be used to prepare and to follow the kinetics of liposome formation whether using a batch/flow or a continuous flow manufacturing process. Moreover, the use of a servo-loop which controls selected manufacturing parameters such as flow rate and/or temperature in accordance with the output of the optical moni-

SUMMARY OF THE INVENTION

The present invention relates to an apparatus for manufacturing liposomes in either batch/flow or continuous flow modes. A liposome precursor solution such as a mixed micelle solution is disposed either within a reaction housing having a reaction chamber therein (in a batch/flow process) or flowable through and along a predetermined flow path counter to the flow of dialysis buffer (in a continuous flow process). In either case a membrane forming a permeable barrier is disposed across the open end of the reaction chamber in the batch/flow instance or along some boundary of the flow path in the continuous flow instance. A dialysis gradient sufficient to initiate liposome formation is defined by a dialysis buffer solution provided on the side of the membrane opposite from the liposome precursor solution. Means for optically monitoring the light transmission level of the liposome precursor solution, for providing light transmission level checks as a function of time, and for generating a signal when the light transmission level reaches a predetermined stable level are provided. The reaching of the predetermined stable level for a predetermined time period indicates the completion of the liposome formation process. The signal output from the optical monitoring means may also be used to provide a real-time indication regarding the concentration of liposomes being formed. Such information can be used as a control input to a feedback control system to control various manufacturing parameters such as the flow rates of both the precursor and the buffer solutions and the temperatures thereof.

In another aspect the invention relates to a continuous counter flow apparatus for manufacturing liposomes.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
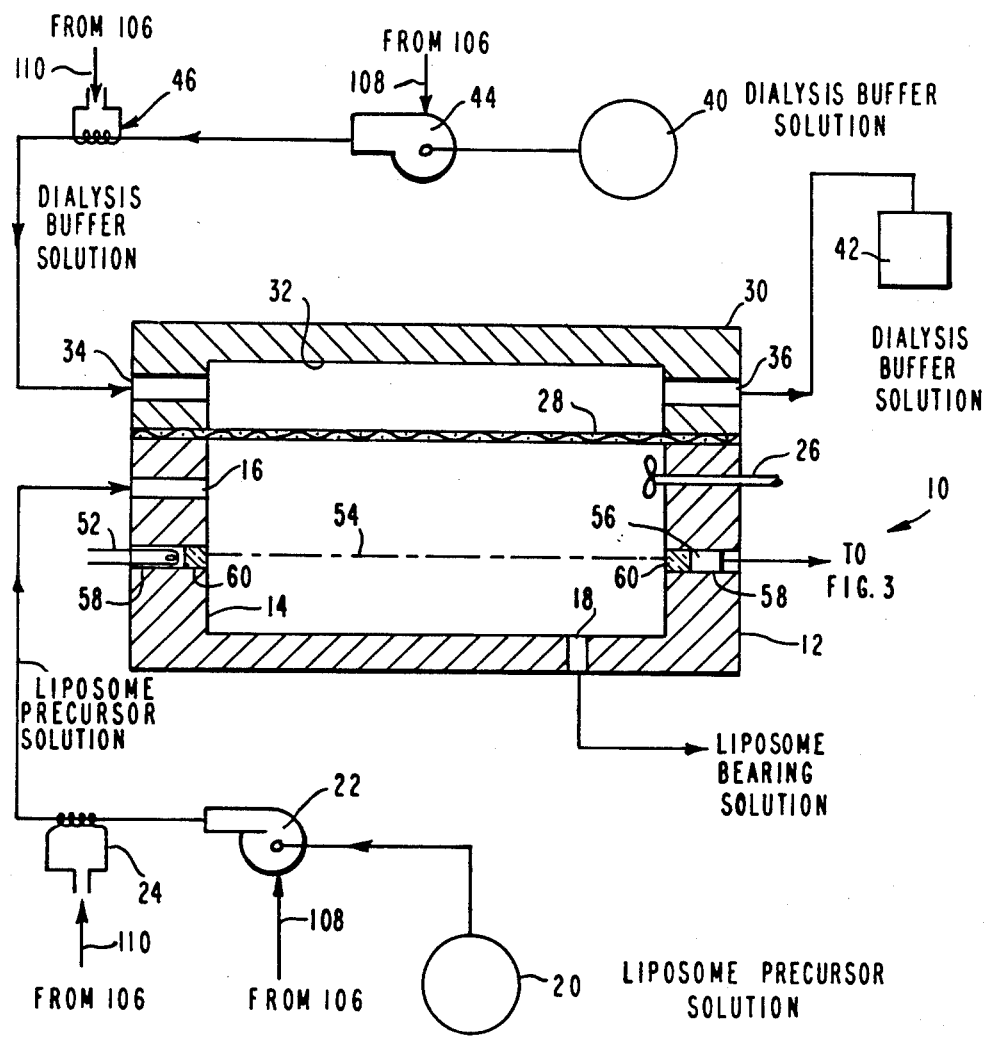
FIG. 1 is a highly stylized pictorial and schematic representation of an apparatus for forming liposomes in a batch/flow process utilizing the teachings of the present invention.

Throughout the following detailed description similar reference numerals refer to similar elements in all figures of the drawings.

With reference to FIG. 1 shown in a highly stylized pictorial and schematic representation of an apparatus 10 in accordance with the present invention used to produce liposomes by a batch/flow process. An apparatus in accordance with the present invention may exhibit any of a plurality of configurations each of which will include structure operable to provide the function as set forth herein. As will be developed the batch/flow process uses a volume of liposome precursor solution and a dialysis buffer moving with respect thereto. This should be contrasted to the so-called batch dialysis process in which a volume of precursor solution is disposed in a dialysis bag and the bag itself immersed in a volume of dialysis buffer solution. The entire volume of the buffer is periodically changed.

With reference to FIG. 1 the apparatus 10 for manufacturing liposomes by the batch/flow process includes a reaction housing 12 having an internal reaction chamber 14 adapted to receive a predetermined volume of a liposome precursor solution such as mixed micelle solution. A suitable port 16 and an outlet port 18 are provided, respectively, for introducing the precursor solution into and withdrawing liposome bearing solution out of the chamber 14. In practice it may be possible to arrange a single port through the housing 12 through which precursor solution is introduced into and liposome bearing solution withdrawn from the housing 12. The precursor solution is derived from a suitable source 20 thereof and pumped by a pump 22 into the vessel 12. Preferably the precursor solution contains a phospholipid molecule such as phosphatidylcholime. A heater 24 is conveniently positioned in the line intermediate the pump 22 and precursor solution inlet 16. If desired a suitable stirring apparatus such as a magnetic or rigid stirring bar 26 may be incorporated into the housing 12 and project into the chamber 14.

The open end of the reaction chamber 14 is covered by a dialysis membrane 28. Suitable for use as a membrane 28 is that sold by Spectrum Medical Industries, Inc., Los Angles, Calif., under the trademark SPECTRAPOR, having a molecular weight cut-off of six thousand to eight thousand.

A top block 30 having a flow channel 32 extending therethrough is suitably secured by any convenient means of attachment to the reaction housing 12. A dialysis buffer solution flow inlet port 34 and an outlet port 36 are provided in the block 30 and are respectively connected to a source 40 of a dialysis buffer solution and to a pump 42. A pump 44 is connected (in either a pressure or suction location) in the dialysis buffer flow loop to initiate and maintain a flow of dialysis buffer solution across that side of the membrane 28 opposite the volume of the liposome precursor solution. The buffer solution is heated by a suitable heater 46.

An optical arrangement for monitoring the light transmission of the solution in the chamber 14 includes a source 52 of interrogating radiation disposed along an optical axis 54 in cooperative association with a photoreceptor 56. The axis 54 is conveniently arranged in any manner or orientation to pass through some portion of the chamber 14 having the precursor/liposome bearing solution therein. The source 52 and receptor 56 are conveniently disposed in suitable apertures 58 located in the reaction housing 12. Windows 60 maintain the integrity of the housing 12. Suitable for use as the source 52 and the receptor 56 are, respectively a continuous tungsten source or a flash source, such as a light emitting diode, and a silicon photodiode detector.

Figure 2:
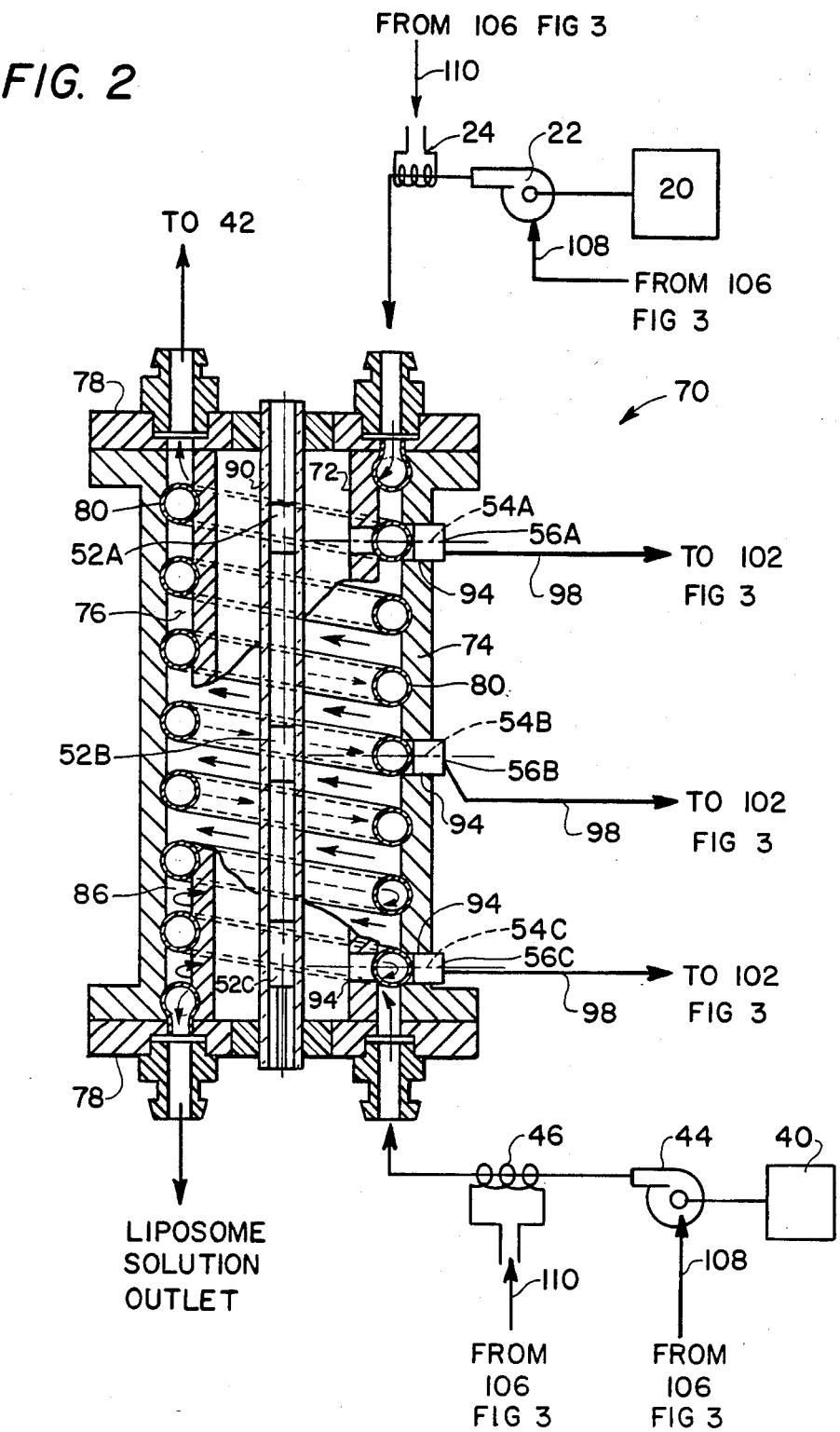
FIG. 2 is a highly stylized pictorial and schematic representation of an apparatus for forming liposomes in a continuous flow process utilizing the teachings of the present invention.

FIG. 2 represents a stylized pictorial representation of an apparatus 70 in accordance with this invention operative for the continuous flow process of manufacture of liposomes. The apparatus 70 includes an in cylindrical member 72 concentrically surrounded by an outer cylindrical member 74 which cooperate to form an annular cavity 76. The cavity 76 is closed at each end by an end plate 78. A tubular structure 80 formed of a dialysis membrane is coiled within the annular space 76. The membraneous tubular structure 80 is supported in the annular space 76 in any convenient manner. For example, the surfaces defining the boundaries of the space 76 may be threaded to receive the structure 80. Respective ends of the coiled tubular membrane 80 are connected as an inlet and outlet of a liposome precursor solution. The liposome precursor solution is pumped through the spiraling tubular structure 80 in the direction of the solid arrows 84.

The exterior of the tubular structure 80 in cooperation with the inner and outer cylindrical members 72, 74 and the end plates 78 cooperate to define an enclosed spiral channel 86 within the annular space 76. This spiral channel 86 is connected to the dialysis buffer flow loop. The dialysis buffer solution is pumped in a counterflow direction as indicated by the dotted arrows 88 with respect to the flow direction of the liposome precursor solution.

It should be appreciated that the precursor solution and the dialysis buffer may be alternated, that is, the dialysis buffer caused to flow within the spiral tubular structure 80 while the liposome precursor flows in the channel 86. It should be noted that other arrangements, not necessarily through a spiraling pattern, may be used to define the necessary counterflow of the precursor and buffer solutions that distinguishes the continuous flow process from the other processes discussed. The spiraling pattern is, of course, preferred because of its desirable volume to height relationship. It should be appreciated that the tubular structure 80 may be fabricated such that only a strip thereof is membraneous.

The formation of liposomes using the continuous counter flow apparatus 70 also may be optically monitored in accordance with this invention. Extending centrally and axially through the interior of the inner member 72 is a central post 90. The post 90 is preferably fabricated of a transparent material and receives the source 52 of interrogating radiation which forms a part of the optical monitoring network in accordance with this embodiment of the invention. Of course, plural sources 52 may be used, if desired. Arrayed axially along the exterior of the outer member 74 is a plurality of photoreceptors 56A, 56B and 56C operationally associated with the source or sources 52 of radiation. Viewing apertures 94 are disposed through the members 72 and 76 such that each receptor is disposed along a respective optical axis 54A, 54B and 54C. Each of the axes 96 passes through a portion of the flow path of the precursor solution at spaced locations along the axis of the apparatus 70. It is noted that the relative positions of the source 52 (or sources) and the photoreceptors 56 may be reversed.

Figure 4:
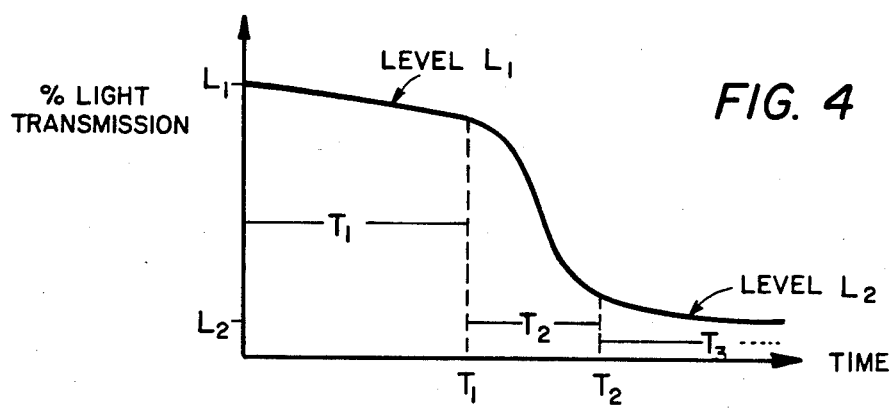
FIG. 4 is a graphical representation of liposome preparation as manifested by the percentage of light transmission (i.e., light transmission level) through the liposome precursor solution as a function of time.

In operation, the flow of dialysis buffer solution on one surface of the membrane 28 (FIG. 1) or 80 (FIG. 2) and of the buffer solution on the other surface of the membrane forms a gradient across the membrane sufficient to initiate migration of detergent out of the liposome precursor solution. As a result, micelle size within the chamber 14 or the tubular structure 80 increases eventually resulting in the production of liposomes. The liposome production process is theoretically explained by the graphical depiction in FIG. 4 which is a representation of liposome formation from a precursor solution as measured by the level of light transmission of the precursor solution (i.e., the percentage of light transmission through the precursor solution) as a function of time. Thus, during an initial time period $T_1$ after production of the gradient across the membrane detergent is removed from the precursor solution but the light transmission therethrough remains substantially at a predetermined initial level $L_1$. This occurs since the micelles are themselves optically transparent. At some point, denoted by the end of time period $T_1$, sufficient detergent is removed from the precursor solution so that thermodynamic rearrangement and coalescence of the micelles occurs to produce unilamellar structures. Such unilamellar structures scatter light, as evidenced by the presently perceived decrease in light transmission of the precursor solution. As a result, light transmission through the precursor solution decreases during the time period $T_2$ from an initial level $L_1$ to a relatively stable level $L_2$. When the light transmission level is relatively stable at the level $L_2$ for a predetermined time period (usually twenty minutes to one hour) practice has indicated that liposome formation is complete.

Figure 3:
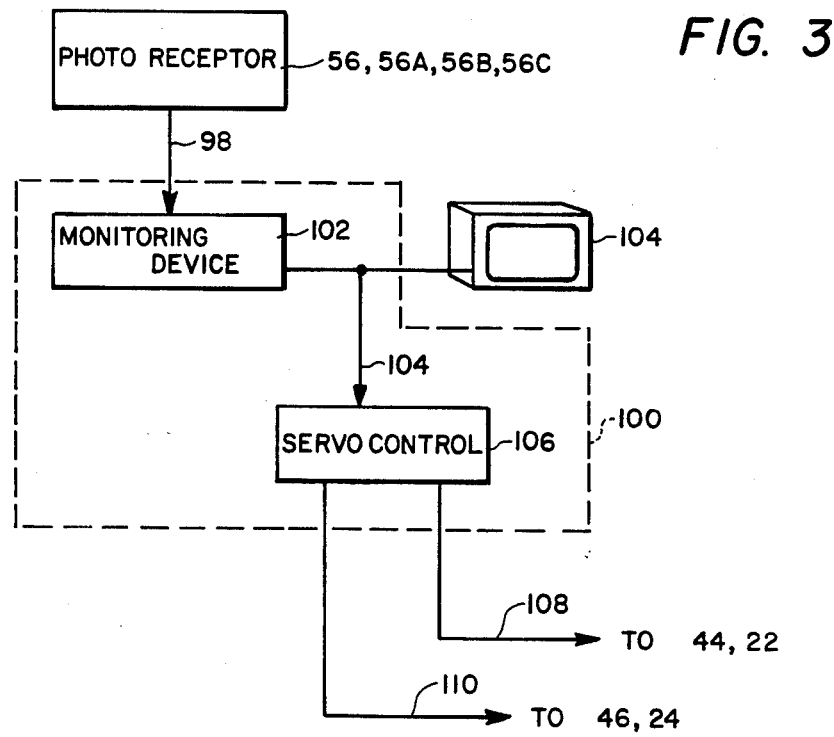
FIG. 3 is a block diagram of a control system usable with either of the apparatus shown in FIGS. 1 and 2.

The present invention utilizes the decrease in light transmission resulting from the formation of unilamellar and multilamellar liposome structures in order to provide a real time signal representative of the kinetics of liposome formation. The signal representation is applied from the photoreceptor(s) 56 (FIG. 1 or FIG. 2) over suitable electrical lines 98 to a monitoring network 100 (FIG. 3).

The signal output from the receptor(s) 56 takes the form of an electrical signal which may be amplified, otherwise buffered and applied via an appropriate interface to a monitoring device 102. The monitoring device 102 may be programmable or may be implemented in hard wire logic. As may be appreciated the output of the receptor(s) 56 is related to the light transmission of the precursor solution and varies over time as liposome structures are formed in the precursor solution. With the light transmission level $L_1$ of the precursor solution as a baseline reference the monitoring device 102 measures the diminution in signal output over time thereby to provide an indication of the formation of the liposomes. The output may be monitored by suitable output device 104 either continuously or at timed intervals to provide a real-time indication of liposome formation. When the output reaches the predetermined stable level $L_2$ during the time period portion $T_3$ of FIG. 4, liposome formation is complete.

In the batch/flow apparatus (FIG. 1) when the level $L_2$ is reached the flow of the dialysis buffer is terminated since liposome formation is completed. In the continuous flow apparatus the attainment of the level $L_2$ is indicative of the fact that the system is balanced and liposomes are forming in the region intersected by the optical axis 56C. It should be understood that information may be obtained if the output signal is at a level other than the level $L_2$. For example, in the continuous flow case, if the signal level from the receptor on the axis 56C remains at the level $L_1$, this provides an indication that a malfunction has occurred (since no liposomes are formed), and accordingly, the flows should be halted. By repeated empirical evaluations using the apparatus disclosed above it may be appreciated that graphical profiles of liposome formation kinetics may be acquired. As a result such acquired information may be used along with the output of the monitoring device 102 and applied as control inputs 1C4 to a control network 106. The network 106 forms a closed loop servo network to control, over appropriate lines 108, either the flow rate of the pump 44 for the dialysis buffer solution or the pump 22 for the liposome precursor solution. The flow rates of these solutions are thereby controlled (or terminated) in accordance with the monitored light transmission of the liposome precursor solution.

Moreover, the precursor solution and/or the buffer solution may be thermally controlled by suitable signals output from the control network 102 via lines 110. The control lines 110 are connected to the heater 24 for the precursor solution and the heater 46 for the buffer solution. In any event, control of the temperature of the precursor and buffer solutions in accordance with the monitored signal output from the monitoring device also lies within the contemplation of the present invention.

Further, detectors may be provided at both the input and output ports of the buffer line in both the batch and the continuous flow cases in order to provide an indication of any membrane rupture or malfunction.

Utilizing the present invention the kinetics of liposome formation can be monitored and/or modified in real time, e.g., for quality control purposes. By being able to monitor the kinetics of liposome formation it is possible, e.g., to define the maximum encapsulation efficiency for a liposome delivery system, to minimize the detergent concentration necessary for liposome formation, to decrease the time required for the onset of liposome formation from hours to minutes, to prepare liposomes consistently and reproducibly, and to produce liposomes which appear to be significantly more stable to 4° C. storage as compared to liposomes prepared using the batch dialysis process.

Those skilled in the art have the benefit of the teaches of the present invention as hereinabove set forth may effect numerous modifications hereto. These modifications are to be construed as lying within the scope of the present invention as defined by the appended claims.

What is claimed is:

1. Apparatus for manufacturing liposomes comprising:
   a reaction chamber adapted to receive a liposome precursor solution:
   a membrane for forming a permeable barrier as one boundary of the reaction chamber, one side of the membrane being communicable with the precursor solution:
   means for conveying a dialysis buffer solution to the other side of the barrier to form a gradient across the membrane; and
   means for optically monitoring the light transmission of the precursor solution for generating a signal representative thereof, the signal containing information regarding the real time kinetics of the formation of liposomes in the solution, the monitoring means comprising a source of radiation and a photosensor both disposed along an optical axis which passes through the precursor solution.

2. Apparatus according to claim 1 further comprising:
   a pump for pumping the dialysis buffer solution, the flow rate of the pump being responsive to the signal representative of the light transmission of the precursor solution.

3. Apparatus according to claim 1 wherein the pump is deactivated to terminate flow of dialysis buffer therethrough when the signal representative of the light transmission of the precursor solution reaches a predetermined stable level for a predetermined time period.

4. Apparatus according to claim 1 further comprising:
   means responsive to the signal representative of the light transmission of the precursor solution for terminating the conveying of the dialysis buffer solution when the signal reaches a predetermined stable level for a predetermined time period.

5. Apparatus according to claim 1 further comprising:
   means responsive to the signal representative of the light transmission of the precursor solution for heating the dialysis buffer solution to a predetermined temperature in accordance therewith.

6. Apparatus for manufacturing liposomes comprising:
   means defining a first flow path through which a liposome precursor solution is flowable in a first direction;
   means defining a second flow path through which a dialysis buffer solution is flowable in a second direction counter to the first direction;
   a membrane disposed along a common interface defined between the means defining the first and second flow paths, the membrane forming a permeable barrier between the counter flows of precursor solution and buffer solution; and
   means for optically monitoring the light transmission of the precursor solution in the first flow path and for generating a signal representative thereof, the signal containing information regarding the real time kinetics of the formation of liposomes in the solution, the monitoring means comprising a source of radiation and a photosensor both disposed along an optical axis which passes through the precursor solution.

7. Apparatus according to claim 6 further comprising:
   means responsive to the signal representative of the light transmission of the precursor solution for controlling the flow of precursor solution in accordance therewith.

8. Apparatus according to claim 7 further comprising:
   means responsive to the signal representative of the light transmission of the precursor solution for heating the buffer solution to a predetermined temperature in accordance therewith.

9. Apparatus according to claim 6 further comprising:
   means responsive to the signal representative of the light transmission of the precursor solution for terminating the flow thereof along the first flow path in the event the signal fails to reach a predetermined stable level after a predetermined time period.

10. Apparatus according to claim 6 further comprising:
    means responsive to the signal representative of the light transmission of the precursor solution for controlling the flow of buffer solution in accordance therewith.

11. Apparatus according to claim 6 further comprising:
    means responsive to the signal representative of the light transmission of the precursor solution for terminating the flow of buffer solution along the second flow path when the signal reaches a predetermined stable level for a predetermined time period.

12. Apparatus according to claim 6 further comprising:

means responsive to the signal representative of the light transmission of the precursor solution for heating the precursor solution to a predetermined temperature in accordance therewith.

13. Apparatus according to claim 7 comprising:

an inner and an outer member concentrically disposed to form an annular space therebetween;

a tubular structure formed of a dialysis membrane coiled within the annular space; and the interior of the tubular structure forming the means defining the first flow path while the exterior of the tubular structure and the inner and outer members cooperating to form the means defining the second flow path.

* * * * *